United States Patent
Bublewitz et al.

(10) Patent No.: US 9,522,368 B2
(45) Date of Patent: Dec. 20, 2016

(54) DOUBLE CARTRIDGE, MIXER THEREFOR AND COMBINATION OF DOUBLE CARTRIDGE AND MIXER

(75) Inventors: Alexander Bublewitz, Herborn (DE); Jens-Peter Reber, Meinerzhagen (DE)

(73) Assignee: Kettenbach GmbH & Co., Eschenburg (DE)

(*) Notice: Subject to any disclaimer, the term of this patent is extended or adjusted under 35 U.S.C. 154(b) by 652 days.

(21) Appl. No.: 13/879,773

(22) PCT Filed: Oct. 26, 2011

(86) PCT No.: PCT/EP2011/068784
§ 371 (c)(1),
(2), (4) Date: Jun. 18, 2013

(87) PCT Pub. No.: WO2012/055926
PCT Pub. Date: May 3, 2012

(65) Prior Publication Data
US 2013/0265846 A1    Oct. 10, 2013

(30) Foreign Application Priority Data

Oct. 26, 2010   (DE) .................. 10 2010 049 378
Feb. 4, 2011    (DE) .................. 20 2011 002 407 U
Aug. 24, 2011   (DE) .................. 10 2011 111 046

(51) Int. Cl.
*B01F 15/02*    (2006.01)
*B01F 7/00*     (2006.01)
(Continued)

(52) U.S. Cl.
CPC ...... *B01F 15/0227* (2013.01); *A61M 5/31596* (2013.01); *B01F 7/00125* (2013.01);
(Continued)

(58) Field of Classification Search
CPC ............ B01F 15/0087; B01F 15/00928; B01F 15/0227; A61M 5/31596; B05C 17/00506; B05C 17/00553; B65D 81/325
(Continued)

(56) References Cited

U.S. PATENT DOCUMENTS 4,046,145 A * 9/1977 Choksi .................. A61J 1/2096
                                                141/2
4,771,919 A * 9/1988 Ernst ..................... B65D 81/325
                                                222/134
(Continued)

FOREIGN PATENT DOCUMENTS

DE        19500782 A1    7/1996
DE    102004030407 A1    1/2006
(Continued)

OTHER PUBLICATIONS

European Office Action issued in European Patent Application No. 11778554.3 dated Oct. 9, 2014.
(Continued)

*Primary Examiner* — Tony G Soohoo
(74) *Attorney, Agent, or Firm* — McDonnell Boehnen Hulbert & Berghoff LLP

(57) ABSTRACT

The invention relates to a double cartridge (1), a mixer (3) and a combination consisting of a double cartridge having a mixer. The cartridge has a guiding channel (14b) that is formed between protrusions (14, 14a; 1a). The mixer (3) has at least one guiding rib (13) to guide the mixer (3) in the double cartridge (1).

13 Claims, 11 Drawing Sheets

Figure 1:
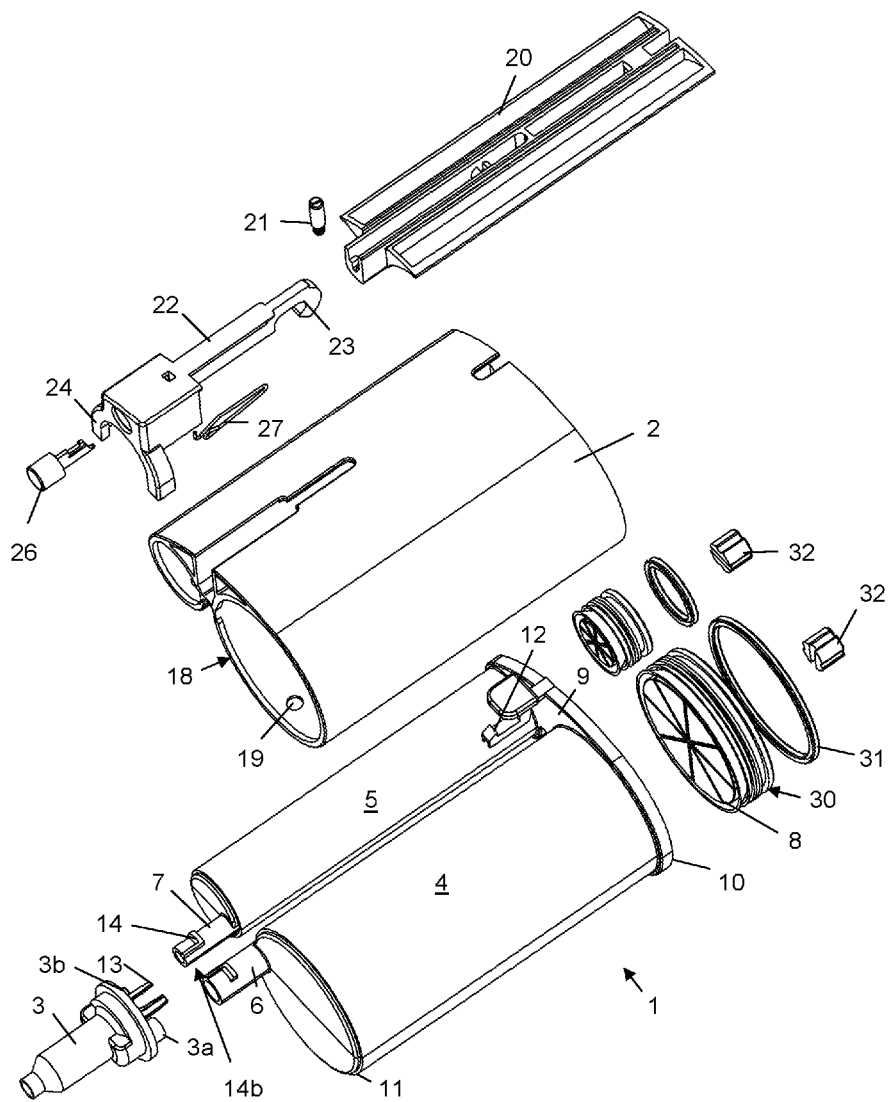

(51) Int. Cl.
      B05C 17/005    (2006.01)
      B65D 81/32     (2006.01)
      A61M 5/315     (2006.01)
      B01F 15/00     (2006.01)
(52) U.S. Cl.
      CPC ...... *B01F 7/00141* (2013.01); *B01F 7/00216*
           (2013.01); *B01F 7/00258* (2013.01); *B01F*
           *15/0087* (2013.01); *B01F 15/00928* (2013.01);
           *B05C 17/00506* (2013.01); *B05C 17/00553*
           (2013.01); *B05C 17/00576* (2013.01); *B65D*
           *81/325* (2013.01)
(58) Field of Classification Search
      USPC ........................................ 604/174, 187, 296
      See application file for complete search history.

(56)         References Cited

U.S. PATENT DOCUMENTS

| | | | |
|---|---|---|---|
| 4,871,090 A    | 10/1989  | Hoffmann     | |
| 4,898,588 A *  | 2/1990   | Roberts      | A61M 3/0287 |
|                |          |              | 604/187 |
| 4,974,756 A *  | 12/1990  | Pearson      | B65D 81/325 |
|                |          |              | 222/137 |
| 4,981,241 A    | 1/1991   | Keller       | |
| 5,228,599 A *  | 7/1993   | Keller       | B05C 17/00513 |
|                |          |              | 222/137 |
| 5,249,709 A *  | 10/1993  | Duckworth    | B05C 17/00506 |
|                |          |              | 222/137 |
| 5,290,222 A *  | 3/1994   | Feng         | A61M 39/04 |
|                |          |              | 604/174 |
| 5,328,462 A *  | 7/1994   | Fischer      | A61C 5/064 |
|                |          |              | 604/191 |
| 5,383,858 A *  | 1/1995   | Reilly       | A61M 5/14546 |
|                |          |              | 604/131 |
| 5,413,253 A *  | 5/1995   | Simmen       | B05C 17/00509 |
|                |          |              | 222/137 |
| 5,443,183 A *  | 8/1995   | Jacobsen     | B05C 17/00513 |
|                |          |              | 222/137 |
| 5,535,922 A    | 7/1996   | Maziarz      | |
| 5,643,206 A *  | 7/1997   | Fischer      | A61C 5/064 |
|                |          |              | 604/191 |
| 5,819,988 A *  | 10/1998  | Sawhney      | B65D 81/325 |
|                |          |              | 222/137 |
| 5,875,928 A    | 3/1999   | Muller et al. | |
| 5,918,772 A *  | 7/1999   | Keller       | B05C 17/00506 |
|                |          |              | 222/145.5 |
| 6,065,645 A *  | 5/2000   | Sawhney      | B01F 5/0615 |
|                |          |              | 222/137 |
| 6,135,631 A *  | 10/2000  | Keller       | B01F 5/0615 |
|                |          |              | 222/145.6 |
| 6,309,372 B1 * | 10/2001  | Fischer      | A61C 5/062 |
|                |          |              | 433/90 |
| 6,328,182 B1 * | 12/2001  | Brugner      | B05C 17/00509 |
|                |          |              | 222/137 |
| 6,398,761 B1 * | 6/2002   | Bills        | A61C 5/062 |
|                |          |              | 222/145.5 |
| 6,592,251 B2 * | 7/2003   | Edwards      | B01F 5/0688 |
|                |          |              | 366/130 |
| 6,936,032 B1 * | 8/2005   | Bush, Jr.    | A61M 5/31551 |
|                |          |              | 604/187 |
| 7,115,234 B2 * | 10/2006  | Freitag      | B01J 19/0046 |
|                |          |              | 422/129 |
| 2002/0170926 A1 * | 11/2002 | Horner     | B05C 17/00513 |
|                |          |              | 222/137 |
| 2003/0183659 A1 | 10/2003 | Van Zeeland et al. | |
| 2004/0068234 A1 * | 4/2004 | Martin      | A61B 17/7095 |
|                |          |              | 604/187 |
| 2006/0138166 A1 | 6/2006  | Nehren et al. | |
| 2007/0095865 A1 | 5/2007  | Chick        | |
| 2007/0175921 A1 * | 8/2007 | Keller      | B05C 17/00506 |
|                |          |              | 222/137 |
| 2009/0152300 A1 * | 6/2009 | Hayman      | A61C 5/062 |
|                |          |              | 222/145.6 |
| 2010/0089949 A1 | 4/2010  | Gramann et al. | |
| 2010/0102088 A1 | 4/2010  | Keller       | |
| 2011/0114668 A1 | 5/2011  | Bublewitz et al. | |
| 2012/0179108 A1 * | 7/2012 | Delabie      | A61M 5/347 |
|                |          |              | 604/187 |
| 2014/0198602 A1 * | 7/2014 | Bublewitz    | A61C 5/064 |
|                |          |              | 366/177.1 |

FOREIGN PATENT DOCUMENTS

| | | |
|---|---|---|
| DE | 202006004738 U1 | 6/2006 |
| DE | 102007044983 A1 | 4/2009 |
| EP | 0302819 A2 | 2/1989 |
| EP | 1972387 A2 | 9/2008 |
| EP | 2335641 A1 | 6/2011 |
| WO | 02094681 A1 | 11/2002 |
| WO | 2007098624 A1 | 9/2007 |
| WO | 2008009143 A1 | 1/2008 |
| WO | 2008113196 A1 | 9/2008 |
| WO | 2008130971 A1 | 10/2008 |
| WO | 2009124407 A1 | 10/2009 |
| WO | 2010020061 A1 | 2/2010 |

OTHER PUBLICATIONS

Form PCT/IB/338, Notification of Transmittal of Translation of the International Preliminary Report on Patentability.

* cited by examiner

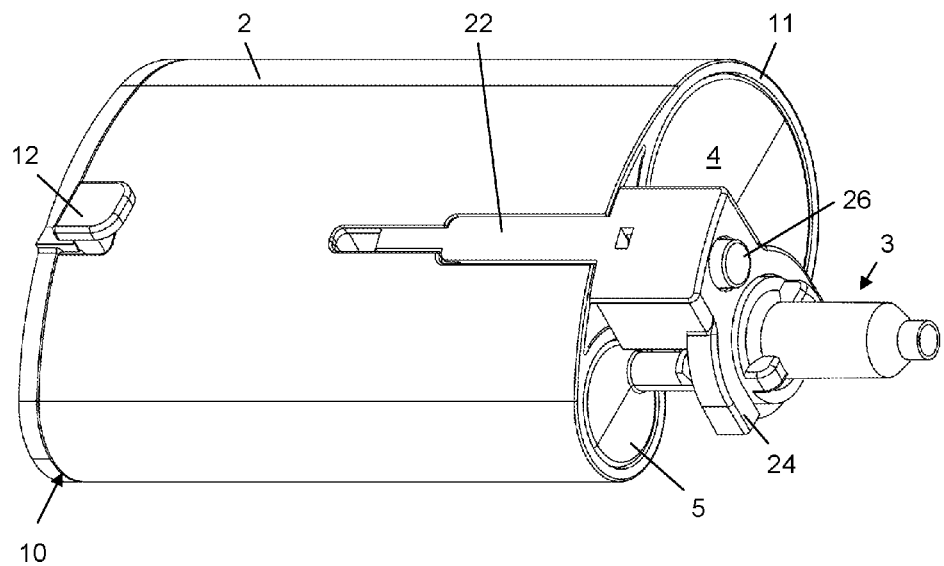
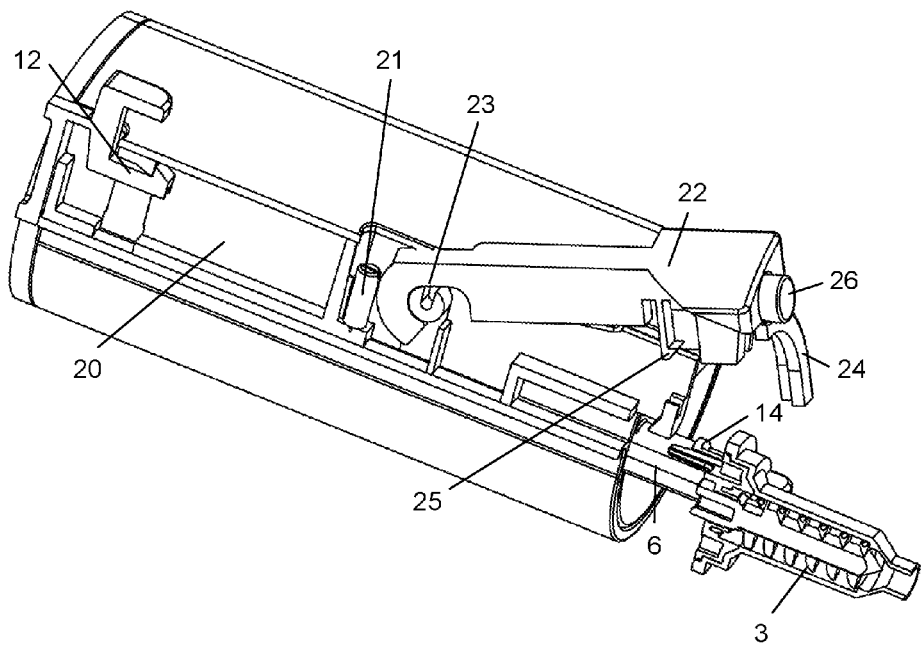

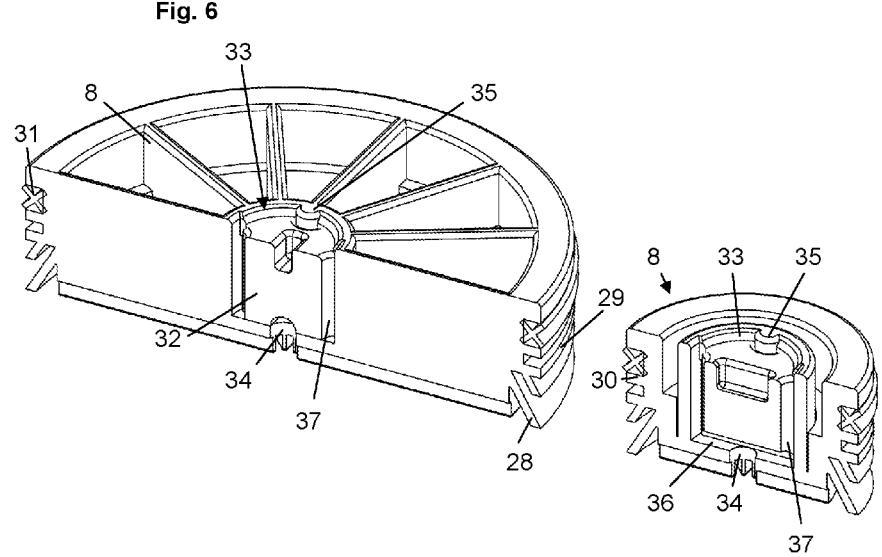
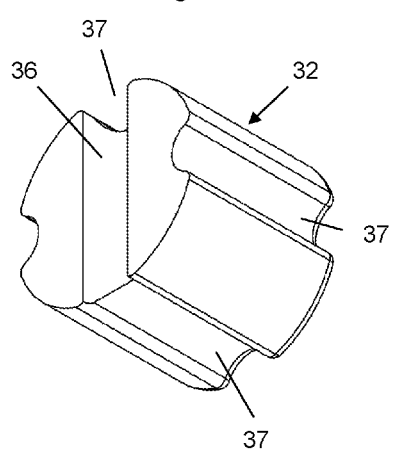
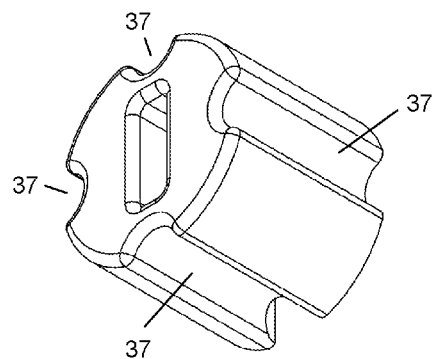

Fig. 20
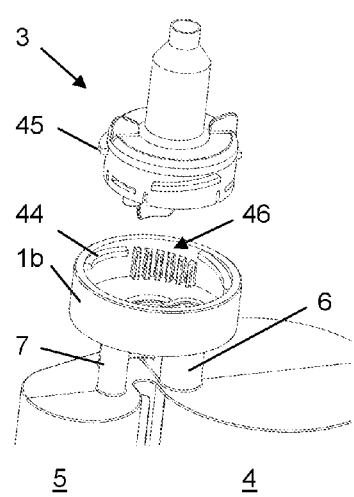
Fig. 21
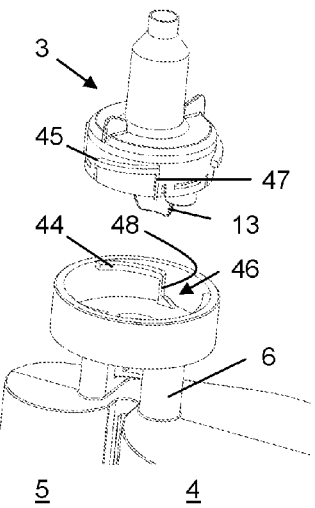
Fig. 22  Fig. 22A  Fig. 23  Fig. 23A
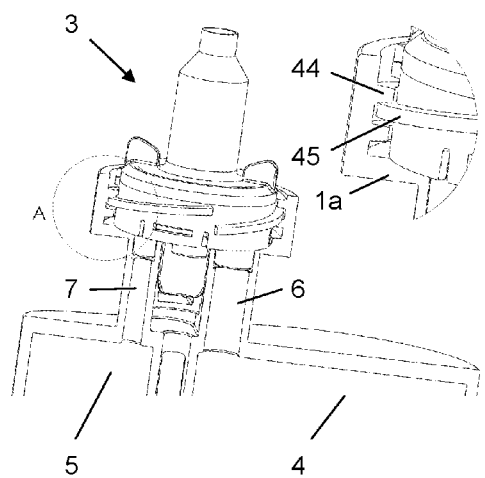
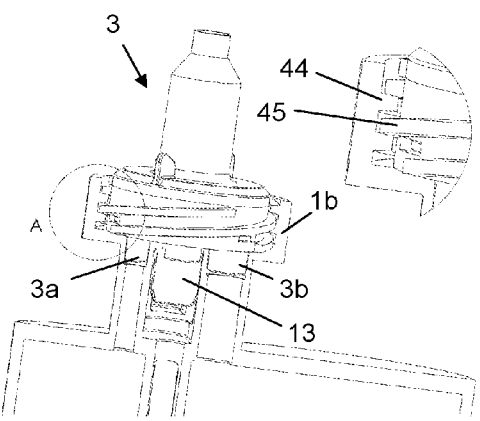

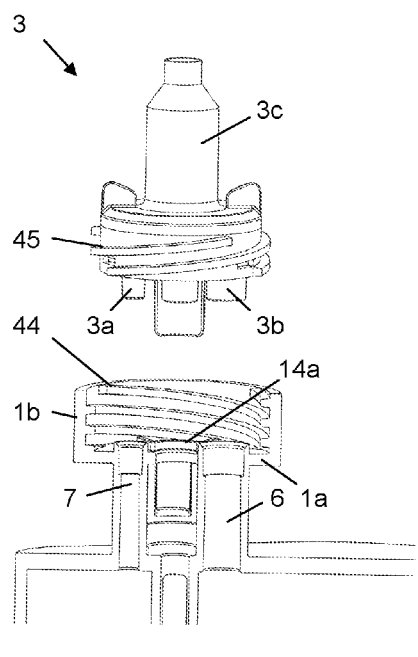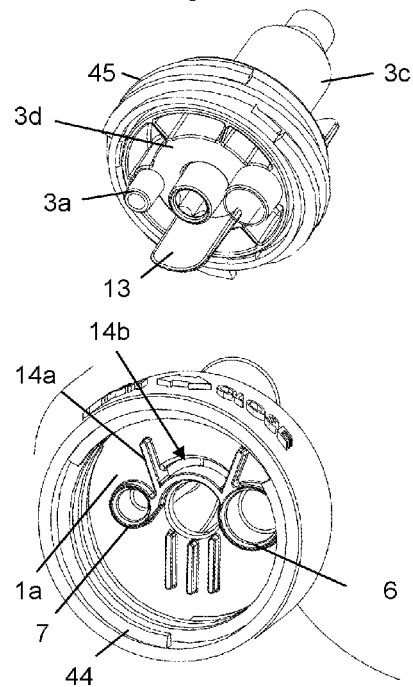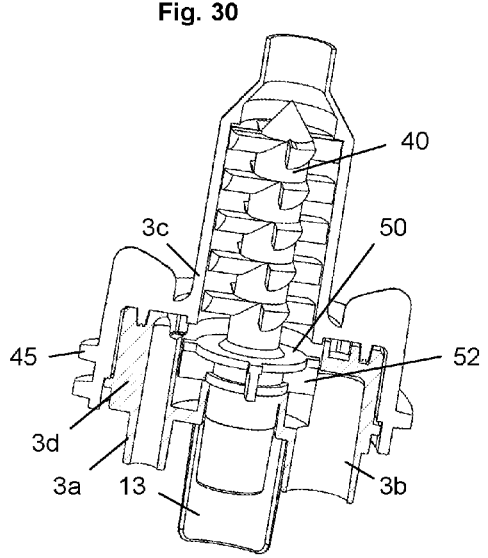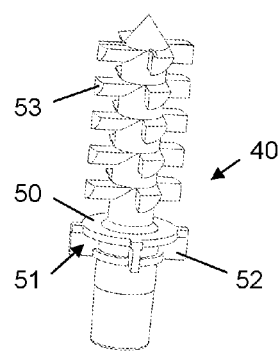

DOUBLE CARTRIDGE, MIXER THEREFOR AND COMBINATION OF DOUBLE CARTRIDGE AND MIXER

CROSS REFERENCE TO RELATED APPLICATIONS

The present application is a 35 U.S.C. 371 National Application of PCT/EP2011/068784 filed Oct. 26, 2011, which claims priority to German Patent Application No. 102010049387.3, filed Oct. 26, 2010 and German Patent Application No. 202011002407.5, filed Feb. 4, 2011 and German Patent Application No. 102011111046.5, filed Aug. 24, 2011, the entire contents of which are incorporated entirely herein by reference.

The invention relates to a double cartridge having two supply containers that respectively have an anterior end with an outlet connection piece, whereby the longitudinal axes of the outlet connection pieces extend at least primarily parallel. Further, the invention relates to a mixer having a housing that defines a mixing chamber, whereby at one outlet end of the housing, an outlet opening and at its diametrically opposite inlet end, two inlet connection pieces are provided that discharge into the mixing chamber, the longitudinal axes of which extend at least substantially parallel. In particular, the mixer can be connected with the double cartridge in order to mix the substances contained in the double cartridge and to deliver the mixture. For this, the inlet connection pieces of the mixer can be connected with the outlet connection pieces of the double cartridge.

These types of systems are used, for example, in dentistry to house and process components for filling materials, filler materials, adhesives or the like. Thereby, the components are stored separate in supply containers and can be discharged through the outlet connection piece into the mixer by a corresponding delivery device using delivery pistons or plungers. The mixer can be a static mixer or a dynamic mixer in which a mixer element is displaced within the housing by a spindle of the delivery device.

In most delivery devices available in the market, the cartridges are retained inclined in such a way that the outlet connection pieces slant downward. This facilitates, for example, filling an impression tray with the mixed components discharging from the mixer. However, it is simultaneously inherent in this configuration that the outlet connection pieces and perhaps the mixing spindle are not easily visible to the user so that the required mounting of a new mixer onto the double cartridge prior to each use is sometimes difficult.

Thus, in EP 2 335 641 A1, a double cartridge and a static mixer that can be connected with it are described, in which the mixer and the double cartridge are fastened by a bayonet connection that is provided on a cap, which surrounds a coupling element that consists primarily of an inlet connection piece and a mixing coil and the mixer housing and can be rotated relative to such. In this mixer, the coupling element is mounted rotatable in the mixer housing. A similar solution is known from WO 2011/041917 A1, whereby the bayonet connection means have a transversely set rotation guide having the effect that during the establishment of the connection, the mixer is inevitably brought close to the cartridge and that while the connection is released, the mixer inevitably lifts off from the cartridge. Prior to this engagement of these (bayonet) connection means, these must first be inserted into each other, whereby coding means ensure that the mixer housing is specifically aligned with the cartridge. In other words, the mixer must first be placed onto the cartridge until the inlet openings of the mixer are connected with the outlet connection pieces of the cartridge before the mixer can be locked by a rotation with the cartridge, for example, by bayonet mounting means designed like a swivel nut.

A specific alignment of the mixer relative to a cartridge is also the subject-matter of EP 0 730 913 A1, which has coding means similar to EP 2 335 641 A1 or WO 2011/041917 A1. However, these coding means are at best suited for aligning a mixer housing or a bayonet ring relative to the cartridge without thereby also inevitably aligning the outlets of the cartridge with the inlets of the mixer.

Thus, in the solutions according to EP 2 335 641 A1 or WO 2011/041917 A1, for example, the connection between the mixer and the cartridge requires a visual control and a precise mounting of the mixer in a predefined position This is sometimes perceived to be cumbersome and impractical. Furthermore, in the mixers according to prior art, a specific alignment of the coupling element relative to the mixer housing is required during the installation of the mixer already, because the mixer could otherwise not be mounted onto the cartridge. This requires an additional costly installation step, including the required quality control. If the coupling element is unintentionally rotated relative to the mixer housing in spite of this prior alignment, the mixer can no longer be mounted on the cartridge, unless these two components are once again previously aligned manually. Furthermore, the bayonet mounting means known from EP 2 335 641 A1 or WO 2011/041917 A1, that engages only at two positions, have been found to be disadvantageous, in particular, at the high delivery pressure that is generated when delivering paste-like masses and/or at high delivery speeds.

Further, there is a combination of a mixer, a bayonet ring like a swivel nut and a cartridge that is offered by Sulzer Mixpac AG (CH-9469 Haag) under product numbers MBD 381-05-00 (mixer), BBD 381-00-11 (bayonet ring) and CBD 381-05-58 (cartridge). A largely similar combination is also described in EP 1 943 012 B1. Hereby, the mixer has a cover or a coupling element that primarily consists of the inlet connection pieces and a mixing coil, a mixer housing and a mixing element that is mounted rotatable in the coupling element.

A coding element projects parallel to the inlet connection pieces of the mixer from the side of the cartridge facing the coupling element, which can engage with clearance with a recess of a plate that is fastened to the outlet connection pieces of the cartridge. The length of the inlet and outlet connection pieces and the coding element are thereby dimensioned in such a way that when the mixer is placed on the cartridge, the inlet connection pieces are already inserted into the outlet connection pieces before the coding element reaches the recess in the plate. Neither the coding element nor the recess in the plate can therefore function as a guide of the mixer when the cartridge is mounted, but merely prevent that the mixer can be locked by the bayonet ring at the cartridge when the mixer is placed on the cartridge rotated by 180°, i.e. the wrong inlet and outlet connection pieces engage. Independent of this, even the large clearance between the coding element and the recess in the plate does not permit any guidance of the mixer at the cartridge.

EP 1 440 737 A1 shows a system having coding means that are designed as guide rails, which engage in recesses that are located at a distance from the cartridge outlets. The coding means can only prevent an incorrect mounting of the mixer without, however, facilitating the placement of the mixer without a visual control.

In contrast, the present invention is based on the objective of providing a double cartridge and a mixer that are easier to connect with each other.

According to the invention, this problem is essentially solved by a double cartridge having the features of claim 1, and a mixer having the features of claim 6. Thereby, the invention is based on the idea of providing guidance independent of the outlet connection pieces and inlet connection pieces of the double cartridge or the mixer that are to be connected with each other that facilitates the exact positioning of the mixer relative to the double cartridge. In other words, the guidance shall ensure that the inlet connection pieces of the mixer can be inserted into the outlet connection pieces of the double cartridge, even if a view of the outlet connection pieces is difficult or not possible because of the location of the delivery device. Thus, even an intuitive, purely tactile finding of the correct mixer position is possible. Thereby, it is particularly preferred, if simultaneously, a possibly provided mixer spindle of the delivery device can also be connected with the mixer.

Concerning this, it is provided according to the invention that on the outer casing surface of the outlet connection pieces of the double cartridge and/or at a plate formed at an outlet connection piece, respectively at least one protrusion is located in such a way that a guiding channel is formed between the protrusions or a protrusion defines a guiding channel that extends at least primarily parallel to the longitudinal axes of the outlet connection pieces. Depending on the size and the alignment of the protrusions, the extent of the guiding channel parallel to the longitudinal axes of the outlet connection pieces can also be very short, for example, if the protrusions are approximately punctiform. This also includes embodiments in which the outlet connection pieces of the cartridge discharge into a plate or are surrounded by a plate, whereby one opening in such a plate then defines the guiding channel. In this case, the thickness of the plate defines the length of the guiding channel. On the side of the plate facing away from the mixer, additional guiding elements can be provided in order to lengthen the length of the guiding channel. Further, the invention is not limited to the design of a single guiding channel, rather, several guiding channels can be formed with which respectively one guiding rib or the like of the mixer can engage. This latterly cited design is suited particularly then, when the outlet connection pieces of the cartridge discharge into a plate, or are surrounded by a plate.

Within the scope of this invention, a double cartridge is, for example, a unit consisting of two integrally connected containers. As an alternative to this, a double cartridge can also be formed by two individual containers, in particular, flexible tube pouches respectively provided with stiff caps, whereby these individual containers can be connected with each other. This can be accomplished, for example, by inserting the containers into two connected tubes that function as support cartridge. Hereby, it is preferred when the individual containers or their caps that respectively have one outlet connection piece for the substances contained in the respective tube pouches or the like, can be aligned with respect to each other in such a way that the protrusions respectively provided on the outer casing surface of the outlet connection pieces are located in such a way that a guiding channel is formed between the protrusions that extends parallel to the longitudinal axes of the outlet connection pieces, in particular, by a corresponding configuration of the support cartridge.

According to a preferred embodiment of the invention, at least one of the protrusions is designed as guiding bar that at least substantially extends parallel to the longitudinal axes of the outlet connection pieces. Hereby, a guiding bar is a protrusion with a primary direction of extension that is aligned essentially parallel to the longitudinal axis of the respective outlet connection piece. These types of guiding bars allow especially good guidance of a mixer that can be connected with the double cartridge, without the risk of tilting the mixer.

As an alternative or in addition to this, at least one of the protrusions can be designed as a cam extending substantially at a right angle to the longitudinal axes of the outlet connection pieces. This makes it possible that the protrusion, in addition to its function of guiding the mixer, also serves as a mounting of the mixer and/or the locking element for the double cartridge, for example, by a snap-in or catch lock.

Preferably, the protrusions are located on the side of the outlet connection pieces facing the user while the double cartridge is in use. In this way, on the first side of the double cartridge, a retaining clip for fixating the mixer at the outlet connection pieces can be provided, whereby the protrusions are then likewise located on this first side of the outlet connection pieces.

With respect to being filled, the stability during the delivery of the components and also with respect to handling, it has been shown to be especially suitable if the double cartridge has a support cartridge in addition to the supply containers, in which the supply containers are preferably housed detachably. Thereby, the support cartridge can be formed by two, in particular, stiffly connected tubes consisting of metal, or a fiber composite material. Hereby, it is possible to produce the supply containers comparably thin-walled and consisting of a cost-effective material and/or a material that can be advantageously processed, because at least the forces acting in the radial direction can essentially be absorbed by the support cartridge.

By way of refining this inventive idea it is provided that the supply containers are at a distance from each other and are integrally connected only at their posterior end by a bridge. In this way it is possible to insert the supply containers of the double cartridge into the support cartridge from a posterior end with respect to the direction of delivery, until the outlet connection pieces protrude out of the support cartridge at the opposite end. The bridge, by means of which the two supply containers are connected, thereby simultaneously serves to support the axial loads acting upon the supply container when delivering the components out of the double cartridge. In addition, the supply containers can also be supported at the anterior end in the support cartridge in the delivery direction.

According to a further embodiment of the invention, the cartridge is provided with a plate or a disk that is located at the outlet connection pieces. Preferably, the outlet connection pieces discharge into this plate or are flush with it. Alternatively, the outlet connection pieces in the direction of the mixer can also project beyond the plate. The plate or disk thus forms, for example, integrally connected protrusions between which a guiding channel can be formed as an opening in the plate. Additionally, further protrusions or bars can be provided on this plate or disk, which likewise contribute the guidance of the mixer. These additional bars can be connected with the outlet connection pieces directly, or can be located at a small distance from such on the plate. The latter can avoid distortions during injection molding.

In a refinement of this embodiment, preferably a ring or similarly flange-like edge is provided at the plate. This ring preferably projects away from the plate in the direction of the mixer and can thereby form an adapter for the cartridge-side end of the mixer. A particularly simple and simultaneously stable mounting of the mixer at the cartridge can be achieved thereby, that the ring has a thread on its inner side, into which an outer thread of the mixer can be screwed.

Independent of the previously cited features, a special aspect of the present invention lies therein, that means are provided at the cartridge that lift or release the mixer from the cartridge, in particular, upon a relative rotational movement of the mixer or mixer housing relative to the cartridge.

This is advantageous, for example, when the mixer adheres or sticks to the cartridge after the mixture has hardened. These types of means for lifting the mixer can, for example, include a threaded connection between the mixer housing and the cartridge so that the mixer also performs an axial relative motion relative to the cartridge when the mixer housing is rotated. Alternatively or in addition to this, one or several inside slopes can be provided at the mixer and/or the cartridge that facilitate lifting off the mixer. In particular, such inside slopes can be provided at a plate into which the outlet connection pieces discharge, and/or at a ring surrounding this plate.

At its inlet end, the mixer according to the invention has at least one guiding rib that extends at least primarily parallel to the longitudinal axes of the inlet connection pieces. In other words, at least one guiding rib projects from the posterior end of the mixer that is facing the double cartridge during use, which can be guided between the protrusions on the outlet connection pieces of the double cartridge in such a way that the inlet connection pieces of the mixer meet the outlet connection pieces of the double cartridge.

If the mixer according to the invention is a dynamic mixer, the movable mixing element of which is connected with a mixer spindle of the delivery device, it has been shown to be especially advantageous if the guiding rib has, in particular, an approximately U-shaped recess. It preferably extends up to an edge of the guiding rib that is facing away from the outlet end. Thereby, the recess prevents that the guiding rib covers the mixer spindle, so that it is possible for a user to continue to check the correct alignment of the mixer spindle to the mixer while the mixer is being mounted. As an alternative to the design of the guiding rib with a recess, it is also possible that two guiding ribs that are at a distance from each other extend away from the backside end of the mixer, so that a recess remains between these two guiding ribs through which a mixer spindle is visible.

When the at least one guiding rib projects over the inlet connection pieces of the mixer, guiding the mixer relative to the double cartridge is possible even before the inlet connection pieces of the mixer come in contact with the outlet connection pieces of the double cartridge. In this way it is possible that a user only needs to align the mixer in such a way that the guiding rib is inserted into the guiding channel formed between the protrusions, in order to be able to mount the mixer on the double cartridge. This makes handling the mixer significantly easier.

The guiding rib of the mixer can also be designed arched or bent. For example, in cross section, the guiding rib can extend perpendicular to the mixer axis almost like a circular segment around the mixer axis.

Independent of the previously cited features it is preferred if the mixer has a housing which can be rotated relative to a cover of the mixer that is provided with the inlet connection pieces. In this design, the mixer housing can be provided with an outer thread in order to make screwing in the mixer possible, for example, into a ring on the cartridge, whereby simultaneously, the inlet connection pieces and the outlet connection pieces interlock A further aspect of the present invention lies therein, that means are provided at the mixer that lift or release the mixer from the cartridge upon a relative motion, in particular, a relative rotation of the mixer or the mixer housing with respect to the cartridge. These types of means for lifting the mixer can, for example, include a threaded connection between the mixer housing and the cartridge and/or inside slopes that can work together with corresponding counter-contours of the cartridge.

Beyond that, the invention relates to a combination consisting of a double cartridge of the type cited above having such a mixer. Such a combination or set means a delivery arrangement that consists of a double cartridge and a mixer that is connected with it or can be detachably connected with it. Thereby, the width of the guiding channel that is formed between the protrusions is preferably coordinated with the width of the guiding rib or the distance of the guiding ribs in the case of two guiding ribs, so that the mixer is guided by the guiding rib(s) and the guiding channel relative to the double cartridge and can be mounted on it. In other words, in the delivery arrangement according to the invention, first the guiding rib(s) of the mixer and the at least one guiding channel of the cartridge join, before, when a mixer is being mounted onto the cartridge, the inlet connection pieces and the outlet connection pieces also interlock.

Figure 4:
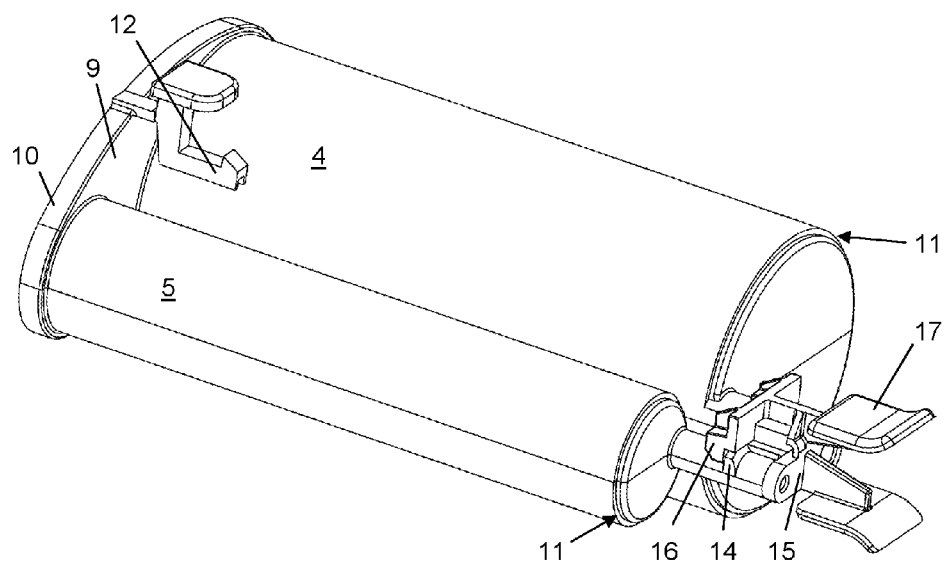
Figure 5B:
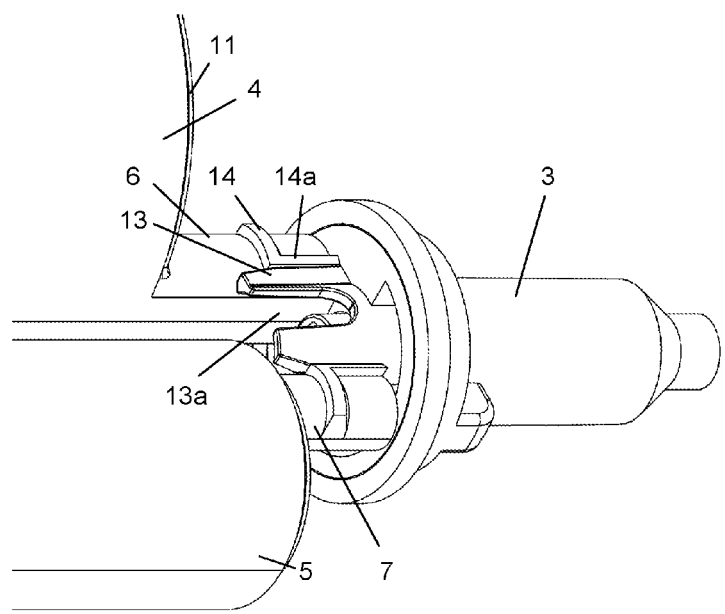
Figure 5A:
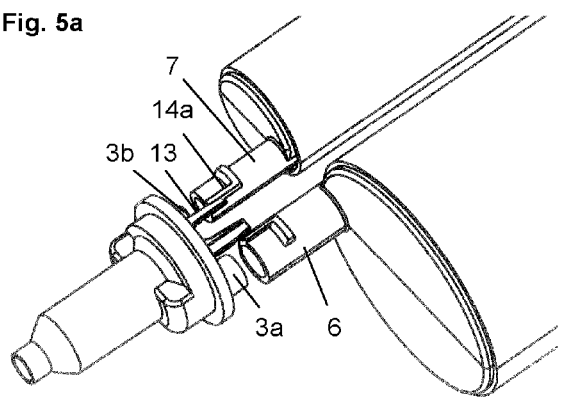
Figure 9:
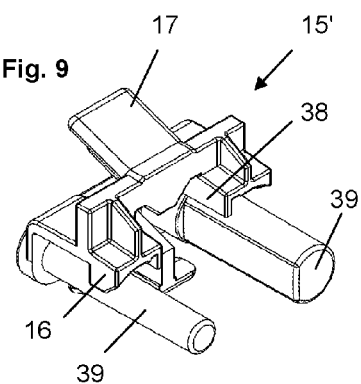
Figure 10:
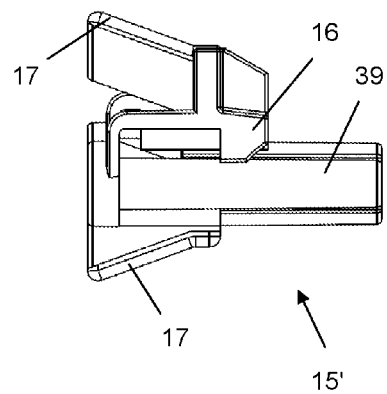
Figure 11:
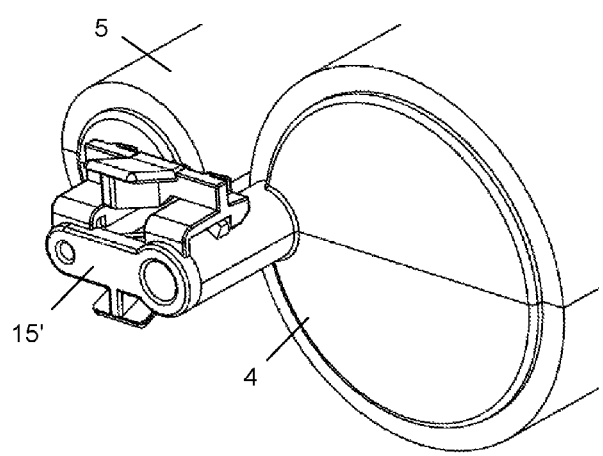
Figure 12:
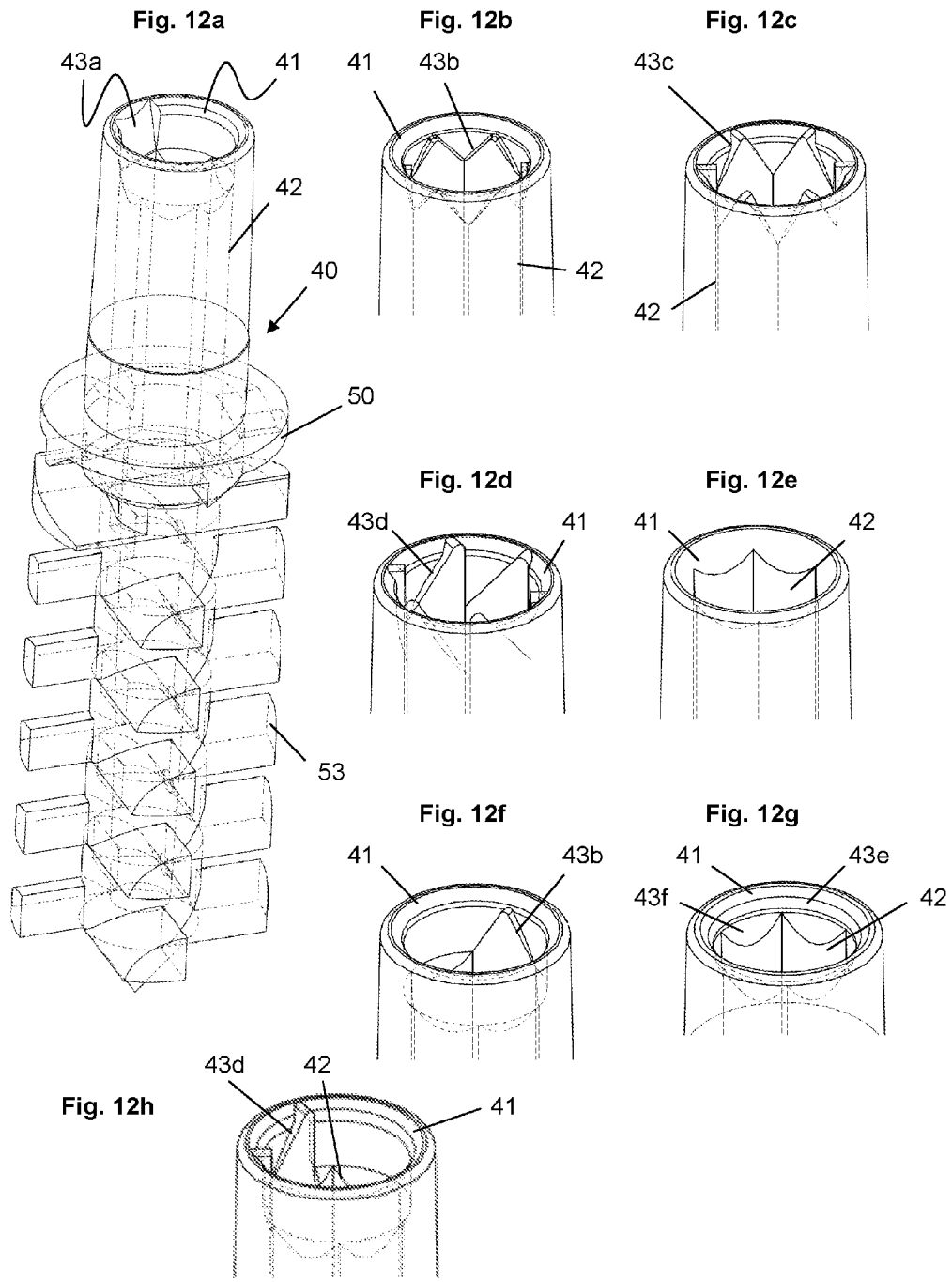
Figure 13:
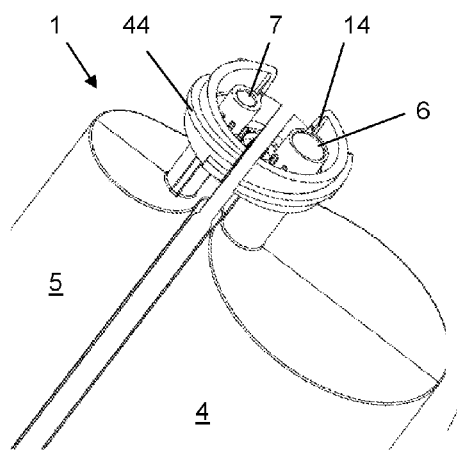
Figure 14:
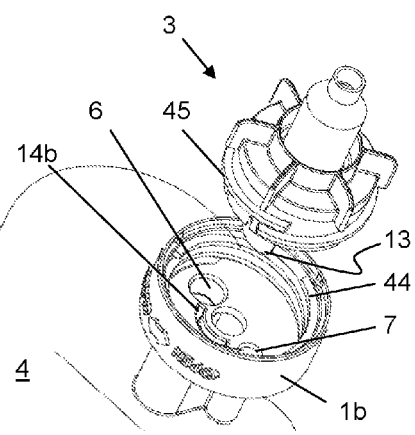
Figure 15:
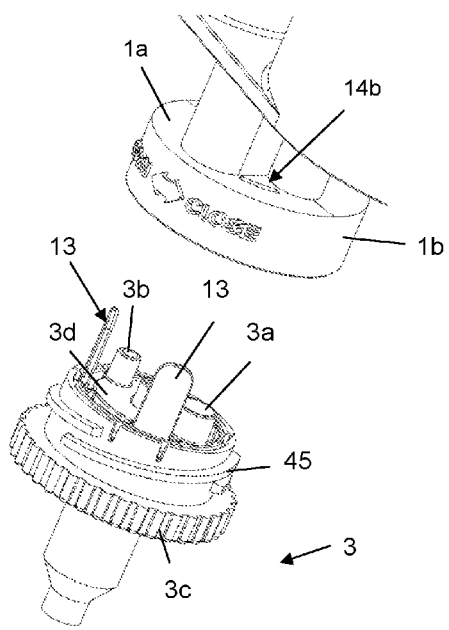
Figure 16:
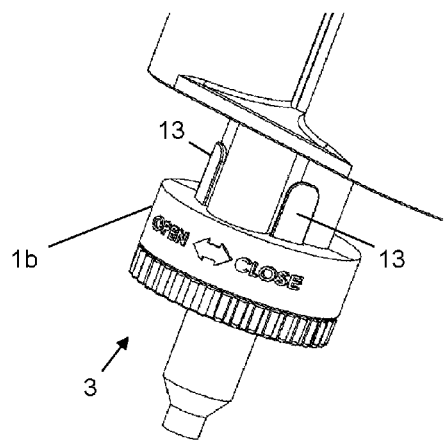
Figure 17:
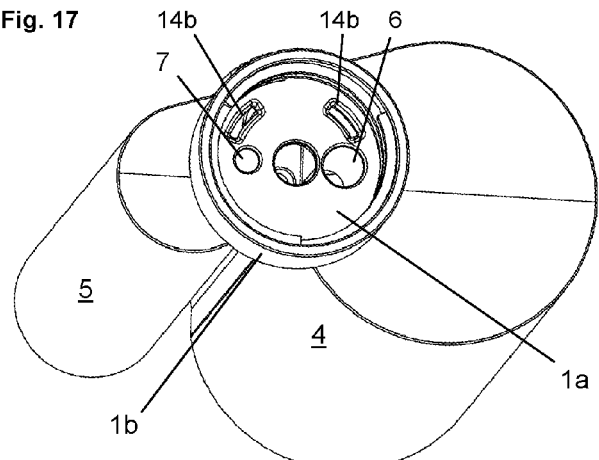
Figure 18:
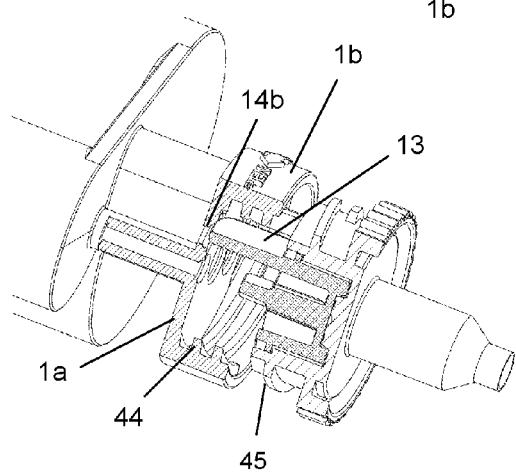
Figure 19:
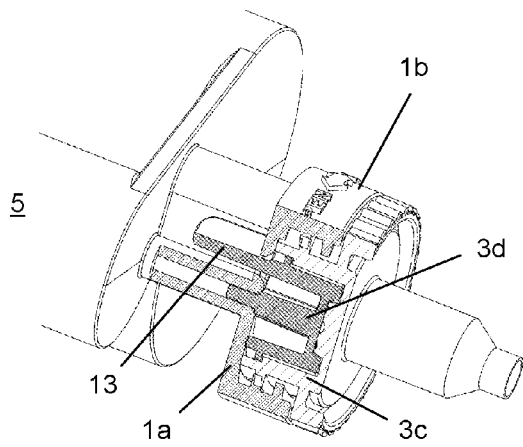
Figure 24:
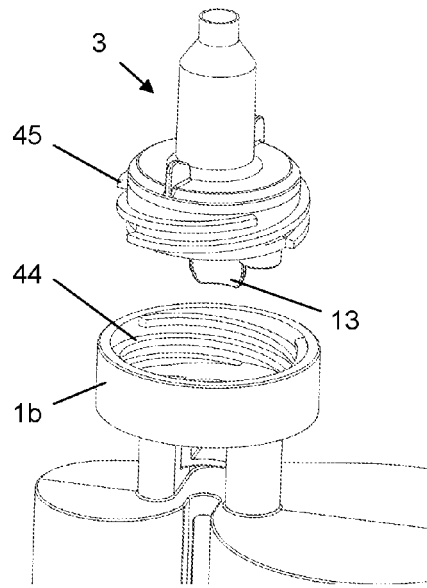
Figure 26:
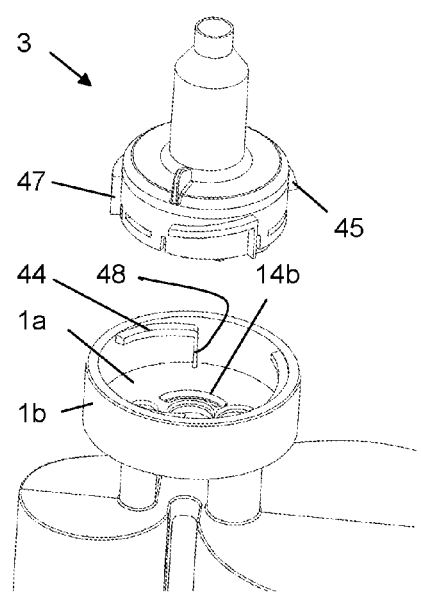
Figure 25:
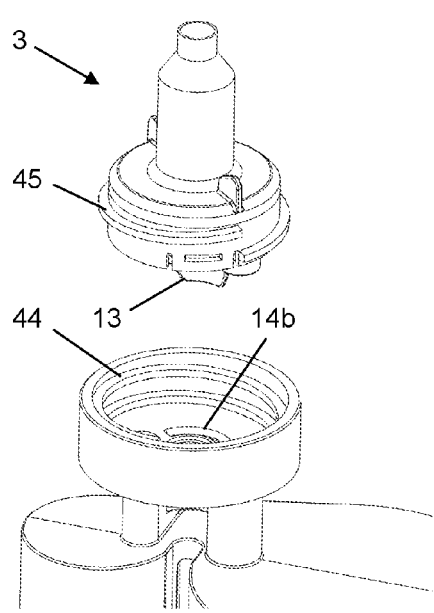
Figure 27A:
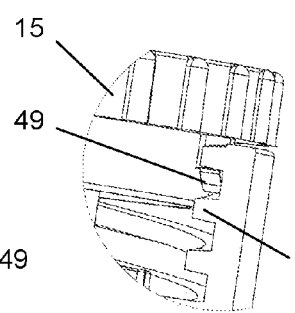
Figure 27:
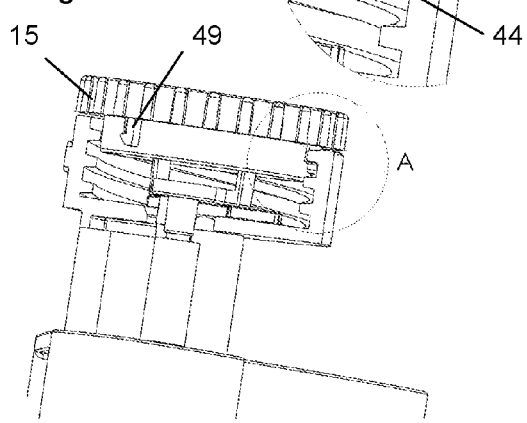

In the following, the invention will be explained in further detail with the aid of an exemplary embodiment and by referring to the drawing. Thereby, all described and/or pictorially illustrated features are the subject-matter of the invention, regardless of their summary in the claims or their references. Schematically shown are:

FIG. 1 shows the components of a cartridge according to the invention in an exploded view, and a mixer according to the invention, FIG. 2 shows the cartridge in a perspective view according to FIG. 1, FIG. 3 shows the cartridge in a partially cross-sectional illustration according to FIG. 1, FIG. 4 shows the cartridge in a perspective view according to FIG. 1 with inserted locking stopper, FIG. 5*a* shows a detail of the cartridge according to FIG. 3 while mounting a mixer, FIG. 5*b* shows a detail of the cartridge according to FIG. 3 with mounted mixer, FIG. 6 shows the delivery pistons of the cartridge according FIG. 1 in cross-sectional view, FIG. 7 shows a turn-lock closure of a delivery piston according to FIG. 6 in a perspective view FIG. 8 shows the turn-lock closure according to FIG. 7 in an additional perspective view, FIG. 9 shows a locking stopper in a perspective view according to a further embodiment, FIG. 10 shows a lateral view of the locking stopper according to FIG. 9, FIG. 11 shows a perspective view of a locking stopper inserted into a double cartridge according to FIG. 9, FIG. 12*a-h* shows a detail of the mixer in an enlarged perspective view, FIG. 13 shows a second embodiment of the double cartridge according to the invention, FIG. 14 shows the third embodiment of a double cartridge according to the invention, FIG. 15 shows a fourth embodiment of a mixer with a cartridge prior to mounting the mixer in a perspective view, FIG. 16 shows the embodiment according to FIG. 15 after mounting the mixer in a perspective view, FIG. 17 shows the cartridge according to FIG. 15 prior to mounting the mixer in a perspective view, FIG. 18 shows a cross-sectional view of the mixer according to FIG. 15 while mounting onto the cartridge, FIG. 19 shows the mixer according to FIG. 15 after mounting onto the cartridge in a cross-sectional view, FIG. 20 shows the fifth embodiment of a mixer with a cartridge prior to mounting the mixer in a perspective view, FIG. 21 shows a sixth embodiment of a mixer with a cartridge prior to mounting the mixer in a perspective view, FIG. 22 shows a seventh embodiment of a mixer with a cartridge while the mixer is being screwed in, in a perspective view, FIG. 22A shows the enlarged detail A from FIG. 22, FIG. 23 shows the mixer according to FIG. 22 while the mixer is being screwed out in a perspective view, FIG. 23A shows the enlarged detail A from FIG. 23, FIG. 24 shows an eighths embodiment of a mixer with a cartridge prior to mounting the mixer in a perspective view, FIG. 25 shows a ninth embodiment of a mixer with a cartridge prior to mounting the mixer in a perspective view, FIG. 26 shows a tenth embodiment of a mixture with a cartridge prior to mounting the mixer in a perspective view, FIG. 27 shows a closure mounted on a cartridge in a partially cross-sectional view, FIG. 27A shows the enlarged detail A from FIG. 27, FIG. 28 shows an eleventh embodiment of a mixer with a cartridge prior to mounting the mixer in a perspective view, FIG. 29 shows the mixer and the cartridge according to FIG. 28 in a further perspective view, FIG. 30 shows a twelfth embodiment of a mixer in a cross-sectional view, and FIG. 31 shows the mixer spindle of the mixer according to FIG. 30 in a perspective view.

The cartridge configuration illustrated in FIG. 1 essentially has one double cartridge 1 and one support cartridge 2. Thereby, double cartridge 1 can be connected detachable with a mixer 3.

As can also be seen in FIGS. 3 and 4, double cartridge 1 essentially consists of two separate supply containers 4, 5, whose housing is essentially cylindrical. The front end of supply containers 4, 5 shown in FIG. 1 on the left is closed by a frontal wall that is dimensioned sufficiently thick to also withstand high forces during delivery of the components. Respectively one outlet connection piece 6 or 7 that forms an outlet opening of the respective supply container projects from this frontal wall. In the illustrated embodiment, outlet connection pieces 6, 7 are located closely adjacent, i.e. not central in the frontal wall of the supply containers. This makes it possible to design mixer 3 comparably compact, as its inlet connection pieces 3a, 3b are not required to have a large distance between them. On the opposite posterior side, supply containers 4, 5 are open so that delivery pistons 8—explained in further detail below—for sealing the supply containers can be inserted. Delivery pistons 8 simultaneously serve to deliver the substances or components of the compression material or the like that is contained in supply containers 4, 5 through outlet connection pieces 6, 7.

At their posterior end, supply containers 4, 5 are connected by a bridge 9. Bridge 9 is designed integral with a flange-like edge 10, which projects over the posterior end of supply containers 4, 5. At the anterior end of the two supply containers 4, 5, a revolving groove 11 is provided in the frontal wall that serves as stop for support cartridge 2.

In the illustrated embodiment, bridge 9 is provided with a catch lever 12, which is designed integral with bridge 9 and supply containers 4, 5. At the anterior end of catch lever 12—in delivery direction—a catch hook is provided whose function will be explained in further detail below.

Outlet connection pieces 6, 7 of supply containers 4, 5 can be connected with mixer 3, which is a dynamic, i.e. an electrically operated mixer in the embodiment that is illustrated. For this, inlet connection pieces 3a, 2b of the mixer are inserted into outlet connection pieces 6, 7. As can also be seen in the detail view in FIG. 5b, a guiding rib 13 is formed at mixer 3, which projects away from the posterior end of mixer 3 toward double cartridge 1. A cam 14 is provided on each outlet connection piece 6, 7, which jointly form a guiding channel 14b, whose width is dimensioned in such a way that guiding rib 13 of mixer 3 is guided between the two cams 14 when mixer 3 is mounted on outlet connection pieces 6, 7. In the embodiment shown, a guiding bar 14a is additionally provided on each outlet connection piece 6, 7 that extends in axial direction and works together with guiding rib 13 of mixer 3. Cams 14 and guiding bars 14a that jointly define guiding channel 14b thus facilitate the precise mounting of mixer 3 by working together with guiding rib 13. The insertion of a mixer spindle of a delivery device into a corresponding adapter of mixer 3—not shown in the Figures—can be facilitated thereby, that in guiding rib 13 of mixer 3 a recess 13a is provided that releases the view of the adapter of mixer 3 that is, for example designed having a hexagonal recess.

The illustration in FIG. 5a shows that guiding rib 13 of mixer 3 is guided in a guiding channel 14b when the mixer is mounted, even before outlet connection pieces 6, 7 come in contact with inlet connection pieces 3a, b. This facilitates the insertion of inlet connection pieces 3a, 3b into outlet connection pieces 6, 7. Beyond that, on outlet connection pieces 6, 7 on the bottom side in FIG. 5a, a barrier or a stop (not shown) can be provided that prevents mounting the mixer rotated by 180°. In other words, such a barrier or stop can prevent that inlet connection piece 3a comes in contact with outlet connection piece 7, or that inlet connection piece 3b comes in contact with outlet connection piece 6. For this, the barriers or the stop are preferably located in such a way that guiding rib 13 of mixer 3 would abut against these before the inlet connection pieces and the outlet connection pieces come in contact.

A further function of cams 14 can be seen in FIG. 4, in which a locking stopper 15 is inserted into the anterior end of double cartridge 1. It has a plate or a bar from which two pins project toward double cartridge 1, which can be inserted into outlet connection pieces 6, 7 in sealing manner. Locking stopper 15 further has catch hooks 16 which engage behind cams 14 on outlet connection pieces 6, 7, when locking stopper 15 locks both outlet connection pieces. To release the interlock, an actuation lug 17 is provided, which can be pulled toward the right in the delivery direction, i.e. in FIG. 4 toward the right, to first release the interlock and then pull locking stopper 15 out of outlet connection pieces 6, 7. As locking stopper 15 simultaneously locks both outlet connection pieces 6, 7, locking stopper 15 also provides stiffening or stabilization of double cartridge 1, the supply containers 4, 5 of which are, for the remainder, connected with each other by bridge 9 exclusively.

In the illustrated embodiment, support cartridge 2 is formed by two integrally connected metal tubes, which are open on both sides. The tubes that consist, for example, of aluminum have a wall thickness of approximately 1 mm to approximately 2 mm, in particular, approximately 1.3 mm. At the left anterior end in FIG. 1, these tubes of support cartridge 2 are provided with an inward-projecting collar 18 at least in sections that can work together with groove 11 of double cartridge 1 to support double cartridge 1 in support cartridge 2. Beyond that, the length of double cartridge 1 is adapted to the length of support cartridge 2 in such a way that that bridge 9 or flange-like edge 10 at the posterior end of double cartridge 1 abuts at the posterior end of the respective tube of support cartridge 2 when double cartridge 1 is inserted into support cartridge 2. As a result, double cartridge 1 is supported and secured in the feed direction of delivery pistons 8 in support cartridge 2 at both of its ends.

Alternative to the illustrated embodiment, support cartridge 2 can be provided with a frontal wall that replaces inward-projecting collar 18, or is supported by ft. Such a frontal wall or plate can also be screwed or glued into support cartridge 2. As the result of a frontal wall, double cartridge 1 is supported even better in support cartridge 2. The wall can either have openings that make the penetration of outlet connection pieces 6, 7 possible, or connection pieces that can house outlet connection pieces 6, 7, can be provided in the wall itself.

Additionally, each tube of support cartridge 2 has a window 19 through which double cartridge 1 is visible from the outside. This also makes it possible to identify, for example, a color marking or similar coding on double cartridge 1 by looking through window 19.

In support cartridge 2, in a section between the two tubes, a slot is provided for receiving an adapter track 20. Adapter track 20 can be inserted into this slot and fixated there by using of a screw 21. Adapter track 20 can, just like support cartridge 2, consist of metal, in particular, aluminum, or preferably, plastic.

Further, support cartridge 2 can be provided with a retaining clip 22, which can be hinged rotatable at a hinge 23 in adapter track 20. Retaining clip 22 has an approximately U-shaped retaining section 24 which can surround mixer 3 in sections and thus mount it on outlet connection pieces 6, 7.

By using a catch hook 25, retaining clip 22 can be fixated in adapter track 20 or in support cartridge 2 in its position that fixates mixer 3. In order to rotate retaining clip 22 out of its interlocked position (FIG. 2) that extends approximately parallel to the tubes of support cartridge 2 into a position releasing mixer 3 (FIG. 3), a release knob 26 is provided that can rotate catch hook 25 into a position releasing the interlock. As the result of a spring 27 indicated in FIG. 1, retaining clip 22 can automatically rotate into the position shown in FIG. 2 after actuating release knob 26, in which an exchange or the installation of mixer 3 is possible. Further, a catch protrusion is provided in adapter track 20 or support cartridge 2 which reaches around catch lever 12 of double cartridge 1 when it is inserted into support cartridge 2. Hereby, double cartridge 1 is also secured against the feed direction of delivery pistons 8 within support cartridge 2. To remove double cartridge 1 from support cartridge 2, a user must apply pressure to the upper section of catch lever 12 to release the interlock again.

As shown in FIG. 6, the delivery pistons are respectively provided with two integrally molded sealing lips 28 and with two ejector bars 29 that revolve around the exterior circumference of the delivery pistons. Additionally, in a revolving groove 30, a gasket ring is housed that can, for example, be designed as an O-ring or as an X-ring. A venting channel extends in each delivery piston 8, which can be sealed by using a turn-lock closure 32. For this, each delivery piston has an essentially cylindrical adapter for a turn-lock closure 32. In FIG. 6, this adapter has a bead 33 at its upper edge that prevents a motion of turn-lock closure 32 in axial direction.

In this way, it is prevented at very high discharge forces of the delivery device (dispenser) and the associated counter pressure of the dental mass that turn-lock closure 32 is again pushed backward axially out of the delivery piston. Otherwise, this would lead to leakage and thus contamination of the delivery device. Alternative to bead 33, a thread or a bayonet connection can also be provided between the adapter and turn-lock closure 32.

The cylindrical adapter is connected with the interior space of supply containers 4, 5 by a vent 34. Further, in the illustrated exemplary embodiment, catch protrusions 35 are provided on the inner side of the cylindrical adapter at two diametrically opposite sides.

Turn-lock closures 33 shown in detail in FIGS. 7 and 8 respectively have a bottom groove 36 on the bottom side in FIG. 6, and four lateral grooves 37 extending in axial direction, of which respectively two are connected with bottom groove 36, while the two remaining lateral grooves 37 are not connected with bottom groove 36. On the side opposite to bottom groove 36, in each turn-lock closure 32, for example, a slot is provided to turn the turn-lock closure in the cylindrical adapter by means of a tool. Catch protrusions 35 on the inside of the cylindrical adapter thereby prevent an unintentional rotation of turn-lock closures 32.

In the delivery piston on the right in FIG. 6, the two lateral grooves 37 that are not connected with bottom groove 36 accept catch protrusions 35, so that via the two lateral grooves 37 that are connected with bottom groove 36, a venting channel is formed that is connected with the interior of supply containers 4, 5 via vent 34. In contrast, in the left delivery piston in FIG. 6, turn-lock closure 32 is rotated by 90°, so that the two lateral grooves 37 that are connected with bottom groove 36 are locked by catch protrusions 35. In this way it is possible to first let the residual air escape from the supply containers after filling supply containers 4, 5 and inserting delivery pistons 8, and to then completely seal the delivery pistons by actuating turn-lock closures 32.

FIGS. 9 to 11 show a further embodiment of a locking stopper 15' in which actuating lugs 17 are offset in the direction toward the cartridge in such a way that actuating lugs 17 essentially do not protrude beyond the end of locking stopper 15' that is facing away from the cartridge. This lessens the risk of damage during transport and decreases the required storage space in the outer packaging. Further, reinforcement elements 38 are provided that surround or house guiding bar 14a in such a way that the torsional stiffness of the double cartridge is improved when locking stopper 15' has been inserted. Further, in FIGS. 9 and 10, protrusions 39 can be seen that engage with the outlet connection pieces which lock the containers of the double cartridge when locking stopper 15' has been inserted.

In the illustrated embodiments, mixer 3 can be mounted on the cartridge system and can be fastened by retaining clip 22. In addition, or as an alternative to this, the mixer can also be provided with an interlocking system that is designed similar to the fastening of locking stoppers 15 or 15'. In other words, even mixer 3 can be provided with catch hooks 16 and an actuation lug 17 for detachable mounting on a cartridge system.

In the Figures, the double cartridge is shown as a single package. Alternatively, individual containers such as tubular pouches that are connected with each other or can be connected with each other can form the double cartridge.

According to a further preferred embodiment, the wall thickness of supply containers 4 or 5 is less than a tenth of the thickness of bridge 9, for example, approximately 0.5 mm to approximately 1.0 mm, preferably approximately 0.7 mm or approximately 0.9 mm. In contrast, the front wall can have a thickness of approximately 7 mm so that it can absorb larger forces.

Furthermore, it is preferred if a revolving groove is formed in the inner side of the front wall, in particular, in the transition section between the front wall and the lateral wall. Hereby, cartridge 1 according to the invention can then also be emptied to the largest degree when (delivery) pistons 8 are used with a radial outer sealing lip 28 pointing in feed direction. Sealing lip 28 can thereby dip into the groove. In addition, the groove offers advantages in injection molding in the transition between the thinner lateral wall and the stronger front wall.

In FIGS. 12a to 12h, various embodiments of the adapter section of a mixer spindle 40 for housing a drive shaft (not shown) are shown. The illustrated inner contours of the adapter sections are intended to respectively facilitate the insertion of a drive shaft with a hexagon head, in particular, when the hexagonal head of the drive shaft is not aligned with an ideal fit for the corresponding counter contour of the receiving section, when the drive shaft is inserted into mixer spindle 40.

For this, FIG. 12a shows mixer spindle 40 of dynamically (drivable) mixer 3 with an annular (tapered) phase 41. For housing a drive shaft (not shown) torque proof, mixer spindle 40 has a hexagonal recess 42, whereby an inside slope 43a is provided that facilitates the insertion of the drive shaft having the hexagonal head. Inside slope 43a slopes inward so that one edge of the hexagonal head of the drive shaft meets this inside slope 43a, the drive shaft on account of continued insertion of the drive shaft into mixer spindle 40 is rotated until one surface of the hexagonal head of the drive shaft abuts at inside slope 43a, i.e. until the hexagonal head is properly aligned with hexagonal recess 42.

Instead of inside slope 43a, in the embodiment according to FIG. 12b, triangles 43b are provided between the annular (tapered) phase 41 and hexagonal recess 42, which facilitate the insertion of the drive shaft having a hexagonal head. Due to the upwardly inclined surfaces of triangles 43 in FIG. 12b, in a possible misalignment of the hexagonal head, it can be rotated by continued insertion of the drive shaft into mixer spindle 40 until the hexagonal head is aligned with hexagonal recess 42.

A similar embodiment is shown in FIG. 12c, whereby instead of triangles 43b, at several positions distributed over the circumference, a tapered inlet 43c is provided respectively. In FIG. 12d, one-sided inlet inclines 43d are provided that allow rotation of the hexagonal head in only one direction. In contrast, in FIG. 12e, the tapered phase 41 is elongated with respect to the previously cited embodiments until it directly forms an incline merging into hexagonal recess 42.

The embodiment of FIG. 12f largely corresponds to FIG. 12b, whereby only one triangle 43b is provided. In the same way, the embodiment of FIG. 12h largely corresponds to that of FIG. 12d, whereby only two saw tooth-like tips 43d are provided which are, however, facing each other with their inclined surfaces.

The embodiment according to FIG. 12g is based on the embodiment of FIG. 12e, whereby subsequent to the tapered phase 41, first a cylindrical guiding section 43e and subsequent to it a further tapered section 43f is provided, which then transitions into hexagonal recess 42.

Hereby, annular phase 41 first centers and guides the drive shaft. Triangles 43 then guide the edges of the hexagonal head of the drive shaft into the hexagonal recess contour 42 of mixer spindle 40 while the mixer is at standstill so that it must rotate a maximum of $\frac{1}{12}$ to receive the hexagonal head.

Different from the previously described embodiments, double cartridge 1 according to the invention can also have a thread 44, which is used for fastening mixer 3. Thereby, in FIG. 13, a double cartridge is shown in which protrusions 14 that are provided on outlet connection pieces 6, 7 are integrally formed with a ring or ring segments that surround both outlet connection pieces. This ring or these ring segments have an outer thread 44 on which, for example, (not shown) a mixer 3 can be mounted by using a coupling nut. A guiding rib 13 of a mixer—likewise not shown—can thereby be guided between protrusions 14 in such a way that the mixer is aligned with the double cartridge in such a way that the inlet connection pieces of the mixer meet the outlet connection pieces of the cartridge.

A similar embodiment is shown in FIG. 14. Hereby the ring or collar 1b at the end of outlet connection pieces 6, 7 is provided with an inner thread 44, into which a corresponding outer thread 45 can be screwed onto the housing of mixer 3. For this, an interior insert of the mixer that also has inlet connection pieces 3a, 3b of the mixer is housed rotatable in the housing of mixer 3, so that the outer housing can be rotated relative to the interior insert for screwing on the mixer.

Collar 1b that carries inner thread 44 can be formed integral with a plate 1a, at which the outlet connection pieces end flush. Protrusions 14 of the two outlet connection pieces 6, 7 thus jointly form plate 1a, whereby guiding rib 13 of the mixer engages with an opening or a guiding channel 14b of the plate in order to align the mixer or its internal insert with the double cartridge in such a way that the inlet connection pieces of the mixer meet the outlet connection pieces of the cartridge. As can be seen in FIG. 14, the width of guiding rib 13 is larger than the diameter of the larger outlet connection piece 6 so that guiding rib 13 cannot accidentally be inserted into an outlet connection piece.

FIGS. 15 to 19 show an embodiment that is similar to FIG. 14, in which instead of a guiding rib 13, two guiding ribs 13 are provided at a distance to each other that can be inserted into an opening or a guiding channel 14b of plate 1a respectively. The tips of guiding ribs 13 can thereby protrude from plate 1a of the cartridge on the side facing away from mixer 3, when the mixer is completely mounted on the cartridge. Hereby, a color marking can also be used to display the mounting of the mixer to the user. As can be seen in the cross-sectional views of FIGS. 18 and 19, independent of the previously described features, a mixer 3 according to the invention is preferably designed with a mixer housing 3c that bears outer thread 45 and forms a coupling section 3d that is freely rotatable—i.e. can be rotated at will in both directions—in which a mixer housing 3c is mounted. Hereby, coupling section 3d has the at least one guiding rib 13 and inlet connection pieces 3a and 3b and locks mixer housing 3c on the cartridge side. Additionally, mixer spindle 40 can be mounted in coupling section 3d. In contrast to known solutions, the free rotatability of the mixer housing relative to the coupling section affords the advantage that the mixer can be mounted on the cartridge in any position and the cartridge and the coupling section can freely align with each other without requiring the user to have direct visual contact, for example, with the inlet connection pieces and/or the guiding rib. In addition, hereby, screwing in the mixer becomes possible, while the inlet and outlet connection pieces and the guiding rib and the guiding channel are already engaged.

The embodiment according to FIG. 20 shows a similar design of mixer 3 with an outer thread 45, whereby the protrusions or bars that form thread 45 extend only around a part of the circumference of the mixer and the individual threaded bar segments do not overlap each other. Rather, free spaces remain between the individual threaded segments. Correspondingly, even for inner thread 44 of the cartridge, only individual threaded segments that do not overlap are provided having free spaces between them. The size of the free spaces is thereby selected in such a way that the threaded segments of the outer thread fit into the free spaces between the segments of the inner thread and the reverse.

While the mixer is being screwed into inner thread 44 of the cartridge, the upper surfaces of the threaded bar segments of outer thread 45 in FIG. 20 abut at the bottom surfaces of the threaded bar segments of inner thread 44 in FIG. 20, in order to draw mixer 3 into ring 1b of the cartridge.

Threads 44, 45 are thereby constructed in such a way that these disengage when mixer 3 is screwed off or out, because the segments of outer thread 45 engaging behind the respective thread segments of inner thread 44 distance themselves from the respective lower surface of the threaded bar segments of inner thread 44. In other words, mixer 3 can at first not be lifted off the cartridge or plate 1a by releasing the threaded engagement into which outlet connection pieces 6, 7 discharge.

But in some cases this is desirable, in particular, when the mixer sticks to the cartridge due to hardening mixtures. For this reason, on the inner wall of ring 1b that surrounds plate 1a of the cartridge, an inside slope 46 is designed that is defined by the head surfaces of several axially extending bars. After the mixer housing is screwed off by a rotation relative to the cartridge until the threaded segments of the two threads no longer overlap, the bottom surfaces of the threaded bar segments of outer thread 45 in FIG. 20 come in contact with the head surfaces of the axial bars, i.e. with inside slope 46 in order to lift mixer 3 from plate 1a of the cartridge at into which outlet connection pieces 6, 7 discharge.

FIG. 21 shows a modification of the embodiment of FIG. 20, whereby the threaded segments of inner thread 44 and of outer thread 45 are in turn designed with corresponding free spaces. Mixer 3 is then screwed into the ring of the cartridge just like it was explained above relative to FIG. 20. The same applies to releasing the threaded connection, whereby in turn the threaded segments first disengage without lifting the mixer from the plate of the cartridge into which the outlet connection pieces 6, 7 discharge.

In the embodiment according to FIG. 21, at the transition section between ring 1b of the cartridge and plate 1a into which outlet connection pieces 6, 7 discharge, inside slopes 46 are provided that can be respectively connected with the corresponding threaded segment of inner thread 44 by an axially extending bar at the inner wall of ring 1b. From the ends of the threaded segment of outer thread 45, axial bars 47 project in the direction of the cartridge on the outer surface of the mixer housing. The ends on the side of the cartridge (bottom in FIG. 21) of these bars 47 reach up to the cartridge-side edge of the mixer housing, or can extend slightly beyond such. Inside slopes 46 and bars 47 have the effect that after the mixer housing is screwed off by a rotation relative to the cartridge until the threaded segments of the two threads no longer overlap, if the mixer continues to be rotated, the cartridge-side ends of bars 47 come in contact with inside slopes 46 in order to lift mixer 4 off plate 1a of the cartridge. Additionally, even the ring (collar) 1b of the cartridge can be provided with axial bars 48 that work together with bars 47 of mixer 3 in such a way that a rotation of the mixer counter to the direction of threads 44, 45 is only possible until mixer 3 can be removed from the cartridge, or is lifted off by inside slope 46.

A further embodiment is shown in FIGS. 22 to 23A. The fundamental structure of the cartridge and the mixer thereby substantially corresponds to the embodiment shown in FIG. 14. In contrast to it, threads 44, 45 on the mixer housing or in ring 1b of the cartridge are, however, designed in such a way that the thread turns, i.e. the free spaces between the threaded segments protruding from the inner wall of ring 1b or from the outer wall of the mixer housing are selected broader than the width of the threaded segments. For example, the thread turns can have a width of approximately 2.3 mm, while the threaded segments only have a width of 1.55 mm. Hereby, a clearance, or a free space is created between the individual threaded segments so that when mixer 3 is screwed into ring 1b of the cartridge (FIGS. 22 and 22A), only the upper surfaces of the threaded segments of outer thread 45 in the Figures abut at the lower surfaces of the threaded segments of inner thread 44 in the Figures in order to pull mixer 3 into ring 1b of the cartridge. Conversely, while screwing mixer 3 off or out (FIGS. 23 and 23A) only the lower surfaces of the threaded bar segments of outer thread 45 in the Figures abut at the upper surfaces of the threaded segments of inner thread 44 in the figures. As a result, the frictional resistance is significantly reduced.

Additionally, the outer diameter of the threaded segments of the outer thread can be defined smaller than the inner diameter of ring 1b in the thread turns and the inner diameter of the threaded segments of the inner thread defined larger than the outer diameter of the mixer housing. As shown in FIGS. 22 to 23A, hereby a radial clearance is also created in the section of threads 44, 45 between ring 1b of the cartridge and the mixer housing, so that mixer 3 is guided in the cartridge exclusively by guiding rib(s) 13 and guiding channel 14b, before inlet connection pieces 3a, 3b and outlet connection pieces 6, 7 also engage. This design of the thread consequently avoids double fits and the forces required for screwing in and for screwing out can be reduced further.

In the embodiment of FIGS. 22 to 23A, the end of threaded segment 45 of mixer 3 that is facing the cartridge does not reach up to the edge of the mixer housing on the cartridge side. As a result of this, a cylindrical section is created at the end of the mixer housing on the cartridge side that does not bear a thread. This section can be used for guiding the mixer housing in addition to the guidance by the guiding rib(s) 13 and guiding channel 14b within the ring or the flange-like edge 1b of the cartridge in which inner thread 44 is located.

As an alternative to this, it is possible according to the invention, to do without such an additional guidance so that while mixer 3 is being mounted on double cartridge 1, the mixer is first exclusively guided and aligned by the at least one guiding rib 13 that engages with guiding channel 14b.

For this, outer thread 45 of the mixer housing can go up to the edge of the mixer housing on the cartridge side. This is shown in the embodiments in FIGS. 24 and 25, whereby the mixer in FIG. 24 has three threaded bar segments that sometimes overlap, which respectively extend approximately 120°, while the mixer according to FIG. 25 has two threaded bar segments that do not overlap, which respectively extend approximately 180°. According to the invention, in the mixers as per FIGS. 24 and 25, the contact between threads 44, 45 while screwing in or screwing out the mixer, as was explained relative to FIGS. 22 and 23A, can also take place with low friction, whereby respectively only one surface of the threads make contact.

A further embodiment is shown in FIG. 26, the structure of which substantially corresponds to the embodiment in FIG. 21. However, in the cartridge in FIG. 26, inside slope 46 in the transition section between plate 1a into which outlet connection pieces 6, 7 discharge and ring 1b or the flange that bears inner thread 44 are omitted, so that mixer 3, although it can be unlocked by such by a rotation of the mixer housing relative to the cartridge, the mixer, however, is not lifted from the cartridge by continued rotation. Rather, mixer 3 must be pulled off the cartridge via threads 44, 45 after the interlock with the cartridge is released. In FIG. 26 as well, the additional axial bars 48 on the inner side of ring 1b are shown that limit—together with bars 47—the rotatability of mixer 3 relative to the cartridge when releasing the connection.

A further locking stopper 15 is shown in FIGS. 27 and 27A that in turn has the protrusions that lock outlet connection pieces 6, 7 and is housed with a cylindrical section within the ring or collar 1b of the cartridge. To interlock locking stopper 15 at the cartridge, hooks 49 are provided that can engage behind the free ends of the threaded bar segments of inner thread 44.

In this way, locking stopper 15 can be snapped onto the cartridge. To release this connection, locking stopper 15 is rotated relative to the cartridge so that hooks 49 release from the threaded bar segments. Simultaneously, the free end of hook 49 on the cartridge side can come in contact with the adjacent (in FIG. 27A bottom) threaded bar segment, so that as a result of the rotation, locking stopper 15 is also lifted off the cartridge.

FIGS. 28 and 29 show a further embodiment that substantially corresponds to FIG. 24, i.e. threads 44, 45 are respectively designed with threaded bar segments that overlap in sections. Fundamentally, outlet connection pieces 6, 7 of a cartridge can also project beyond plate 1a, as is indicated, for example, in FIGS. 28 and 29.

Independent of this, on plate 1a, a guiding protrusion 14a can be formed that facilitates the insertion of guiding rib 13 into slot 14b. In the embodiment shown in FIGS. 28 and 29, this additional guiding protrusion 14a has two funnel-shaped sections facing each other on both sides of guiding slot 14b that are connected with each other by a curved section. Additional guiding protrusion 14a can thereby be either directly connected with outlet connection pieces 6, 7, or located at a small distance from such.

Additionally, ribs can be seen on plate 1a in FIG. 29, which are opposite to guiding slot 14b. These prevent mounting mixer 3 on the cartridge in the wrong direction.

Because of the high pressure that is generated during delivery, the impermeability between the cartridge and the mixer is especially important in modern delivery systems (cartridge, mixer and delivery device for driving the pistons in the cartridge). According to the invention, this is also achieved, for example, in the embodiments of FIGS. 28 and 29 thereby, that by a thread with several thread turns, a large axial relative motion between the mixer and the cartridge is generated during the screwing in process. Hereby, the mixer can be firmly pressed onto the cartridge so that on the one hand, the inlet and outlet connection pieces are connected with each other in a sealing manner, and on the other hand, even within the mixer itself, in particular, between mixer housing 3c and coupling section 3d, the impermeability is improved. Additionally, the thread turns, which are preferably offset by 120° and overlap each other, also absorb the axially occurring forces well. However, this threaded connection also requires that the coupling section and the mixer housing are freely rotatable with respect to each other. This in turn has the effect of simplifying the alignment of the inlet and outlet connection pieces when mounting mixer 3, first the guiding rib engages with the guiding channel and thus guides and aligns the mixer.

FIGS. 30 and 31 show a further aspect of a mixer 3 according to the invention, in which inlet connection pieces 3a, 3b discharge at offset planes into the mixing chamber formed in mixer housing 3c. In other words, the inlet for the mass entering through inlet connection piece 3b is closer to the cartridge than the inlet for the mass entering through inlet connection piece 3a. Hereby, an annular space is formed in the interior of the mixer that surrounds mixer spindle 40, in which the mass entering through inlet connection piece 3b can be captured before it reaches into the mixing chamber. This prevents a bad mixing result at the beginning of the mixing process.

The two planes at which the masses enter are separated from each other by disk 50 on mixer spindle 40, whereby openings 51 permit penetration of the mass entering through inlet connection piece 3b. To make it more difficult that a mass from one inlet connection piece gets into a different one when mixing spindle 40 is at standstill, ribs 51 are provided in the spaces between openings 51.

Mixing blades 53 of the mixer spindle and the remaining embodiment, for example, of the connection section with a drive shaft, can be designed as shown in FIGS. 12a to 12h.

| Reference numbers | |
|---|---|
| 1 | Double cartridge |
| 1a | Plate |
| 1b | Collar |
| 2 | Support cartridge |
| 3 | Mixer |
| 3a, b | Inlet connection piece |
| 3c | Mixer housing |
| 3d | Coupling section |
| 4 | Supply container |
| 5 | Supply container |
| 6 | Outlet connection piece |
| 7 | Outlet connection piece |
| 8 | Delivery piston |
| 9 | Bridge |
| 10 | Flange-like edge |
| 11 | Groove |
| 12 | Catch lever |
| 13 | Guiding rib |
| 13a | Recess |
| 14 | Cam |
| 14a | Guiding bar |
| 14b | Guiding channel |
| 15, 15' | Locking stopper |
| 16 | Catch hook |
| 17 | Actuating lug |
| 18 | Collar |
| 19 | Inspection glass |
| 20 | Adapter track |
| 21 | Screw |
| 22 | Retaining clip |
| 23 | Hinge |
| 24 | Retaining section |
| 25 | Catch hook |
| 26 | Release knob |
| 27 | Spring |
| 28 | Sealing lip |
| 29 | Ejection bar |
| 30 | Groove |
| 31 | Gasket ring |
| 32 | Turn-lock closure |
| 33 | Bead |

| Reference numbers | |
|---|---|
| 34 | Vent |
| 35 | Catch protrusion |
| 36 | Bottom groove |
| 37 | Lateral groove |
| 38 | Stiffener |
| 39 | Protrusion |
| 40 | Mixer spindle |
| 41 | Annular phase |
| 42 | Hexagon socket |
| 43a | Inside slope |
| 43b | Triangle |
| 43c | Inlet |
| 43d | Tip |
| 43e | Cylindrical guide |
| 43f | Annular phase |
| 44 | Inner thread |
| 45 | Outer thread |
| 46 | Inner slope |
| 47 | Bar |
| 48 | Bar |
| 49 | Hook |
| 50 | Disk |
| 51 | Opening |
| 52 | Rib |
| 53 | Mixing blade |

What is claimed is:

1. A combination consisting of a double cartridge having a mixer,
whereby the double cartridge has two supply containers that respectively have an anterior end with an outlet connection piece,
whose longitudinal axes extend parallel and on whose outer casing surface at least one protrusion is located respectively, and
wherein the mixer has a housing that defines a mixing chamber,
whereby at one outlet end of the housing an outlet opening, and at its diametrically opposite inlet end of the mixer two inlet connection pieces discharging into the mixing chamber are provided, whose longitudinal axes extend parallel,
wherein the mixer has an outer helical thread and the double cartridge has an inner thread for mounting the mixer on the double cartridge,
that the at least one protrusion is located in such a way that each of the protrusions jointly form a plate and that between the protrusions at least one guiding channel is formed that is defined by an opening in the plate and that extends parallel to the longitudinal axes of outlet connection pieces,
that at the inlet end of the mixer at least one guiding rib is provided that extends parallel to the longitudinal axes of the inlet connection pieces, and
that at the inlet end at least one interlocking element is formed as an outer thread for detachable mounting to a cartridge system
and that the width of the guiding channel that is formed between protrusions and the width of the at least one guiding rib for guiding the mixer in the double cartridge, are adapted to each other,
wherein the lengths of the inlet connection pieces, of the guiding rib and the outlet connection piece and the position of the protrusions are coordinated in such a way that when the mixer is mounted on the double cartridge,
the guiding rib engages with the guiding channel that is formed between the protrusions, before the inlet connection pieces make contact with the outlet connection pieces.

2. The combination as recited in claim 1,
wherein the width of the guiding rib is larger than the cross section of the opening of the largest outlet connection piece of the double cartridge.

3. The combination as recited in claim 1,
wherein on the plate a guiding protrusion is formed that facilitates the insertion of the guiding rib into the guiding channel that is designed as a slot.

4. The combination as recited in claim 3,
wherein the guiding protrusion has two facing tapered sections that are provided on both sides of the guiding channel and which are connected by a curved section.

5. The combination as recited in claim 3,
wherein the plate has ribs that are opposite to the guiding channel.

6. A mixer comprising
a housing that defines a mixing chamber,
with a drivable mixer spindle that has a hexagonal recess contour for housing a drive shaft in a torque-proof manner,
wherein the mixer spindle is provided with an annular phase and/or triangles transitioning into the hexagonal recess contour at the inlet end,
whereby at one outlet opening of the housing, an outlet opening is provided and at its diametrically opposite inlet end of the mixer two inlet connection pieces discharging into the mixing chamber are provided whose longitudinal axes extent parallel,
wherein at the inlet end, at least one guiding rib is provided that extends parallel to the longitudinal axes of the inlet connection pieces, and
that at the inlet end at least one interlocking element is formed as an outer thread for detachable mounting to a cartridge system.

7. The mixer as recited in claim 6,
wherein the outer thread is formed by several non-overlapping threaded bar segments.

8. The mixer as recited in claim 6,
wherein the lengths of the inlet connection pieces are shorter in a direction facing away from the outlet end than the length of the at least one guiding rib.

9. The mixer as recited in claim 6,
wherein the inlet connection pieces and the at least one guiding rib are components of a coupling section of the mixer that is housed freely rotatable in a mixer housing.

10. The mixer as recited in claim 6,
wherein the inlet connection pieces discharge in offset planes into the mixing chamber that is formed in the mixer housing.

11. The mixer as recited in claim 10
with a drivable mixer spindle,
wherein the two planes at which the masses enter are separated by a disk on the mixer spindle,
whereby openings permit the penetration of the mass entering through one of the inlet connection pieces.

12. The mixer as recited in claim 11,
wherein ribs are provided between said openings in said plate.

13. The mixer as recited in claim 6 with a drivable mixer spindle,
wherein an annular space is formed in the interior of mixer that surrounds the mixer spindle in which the mass entering through one of the inlet connection pieces can be captured before it reaches into the mixing chamber.

* * * * *